(12) United States Patent
Callsen et al.

(10) Patent No.: US 6,640,810 B1
(45) Date of Patent: Nov. 4, 2003

(54) FOOT PROTECTOR

(75) Inventors: Kevin Callsen, Cleveland, OH (US); Terri Wade, Lakewood, OH (US); Patrick S. Baran, Cleveland, OH (US)

(73) Assignee: Polymer Concepts, Inc., Mentor, OH (US)

( * ) Notice: Subject to any disclaimer, the term of this patent is extended or adjusted under 35 U.S.C. 154(b) by 0 days.

(21) Appl. No.: 10/177,471

(22) Filed: Jun. 21, 2002

Related U.S. Application Data

(60) Provisional application No. 60/300,213, filed on Jun. 22, 2001.

(51) Int. Cl.[7] .................................................. A61F 5/37
(52) U.S. Cl. ....................................................... 128/882
(58) Field of Search ................................ 128/846, 882; 602/23, 27, 28, 60, 61, 62; 5/630, 648, 651; D24/190, 192

(56) References Cited

U.S. PATENT DOCUMENTS

| | | |
|---|---|---|
| 3,511,233 A | 5/1970 | Holy, Jr. |
| 3,691,658 A | 9/1972 | Di Perno et al. |
| 3,901,228 A | 8/1975 | Brown |
| 3,936,959 A | 2/1976 | Hanson et al. |
| 4,076,022 A | 2/1978 | Walker |
| 4,104,746 A | 8/1978 | Goetz |
| 4,150,442 A | 4/1979 | Boone |
| 4,186,738 A | 2/1980 | Schleicher et al. |
| 4,197,845 A | 4/1980 | Browning |
| 4,266,298 A | 5/1981 | Graziano |
| 4,278,079 A | 7/1981 | Simhoni et al. |
| 4,294,022 A | 10/1981 | Stockli et al. |
| 4,369,588 A | 1/1983 | Berguer |
| 4,478,214 A | 10/1984 | Lamont |
| RE33,090 E | 10/1989 | Berguer |
| 5,143,058 A | 9/1992 | Luber et al. |
| 5,226,245 A | 7/1993 | Lamont |
| 5,269,748 A | 12/1993 | Lonardo |
| 5,298,013 A | 3/1994 | Lonardo |

(List continued on next page.)

OTHER PUBLICATIONS

EHOB Inc., Waffle Brand Lower Limb Air Cushions, copyright 1995.
Kinetic Concepts, Inc., RIK: The RIK FootHugger is a multi-user fluid heel boot for pressure and shear relief, copyright 2000.

(List continued on next page.)

*Primary Examiner*—Michael A. Brown
(74) *Attorney, Agent, or Firm*—Pearne & Gordon LLP

(57) ABSTRACT

A foot protector to be worn on the foot of a bedridden patient. The foot protector has a fabric body, a top opening for exposing an anterior portion of the patient's foot and lower leg, a strap for partially closing the top opening, a fastener for securing the strap, a bottom opening for exposing the heel, and a toe flap adjacent the top opening for alternately supporting and covering the toes. The foot protector also includes a generally wedge-shaped deformable block enclosed within the fabric body for supporting the calf of the patient. The block has a truncated peak forming a plateau for relieving an Achilles region of the patient's foot and a heel relief area. Further, two lower longitudinal edges of the block are chamfered to allow the foot to be rolled from side to side and to prevent the foot from completely flipping sideways.

10 Claims, 3 Drawing Sheets

U.S. PATENT DOCUMENTS

| | | | |
|---|---|---|---|
| 5,328,445 A | 7/1994 | Spahn et al. | |
| 5,367,789 A | 11/1994 | Lamont | |
| 5,449,339 A | 9/1995 | Drennan | |
| 5,453,082 A | 9/1995 | Lamont | |
| 5,571,077 A | 11/1996 | Klearman et al. | |
| 5,584,303 A | 12/1996 | Walle | |
| 5,603,692 A | 2/1997 | Maxwell | |
| 5,665,059 A | 9/1997 | Klearman et al. | |
| 5,745,939 A | 5/1998 | Flick et al. | |
| 5,797,862 A | 8/1998 | Lamont | |
| 5,827,211 A | 10/1998 | Sellinger | |
| D410,746 S | 6/1999 | Klein | |
| 5,957,872 A | 9/1999 | Flick | |
| 5,957,874 A | 9/1999 | Klein | |
| 5,997,491 A | 12/1999 | Harris | |
| 6,083,185 A | 7/2000 | Lamont | |
| D453,969 S | 2/2002 | Callsen et al. | |

OTHER PUBLICATIONS

DM Systems, Inc., Advances In Skin & Wound Care: Heelift Suspension Boot, Jul./Aug. 2000, p. 149.

AliMed, Nonambulatory leel ulceration protection, p. J26.

AliMed, Treat heel ulcerations in comfort, p. J29.

FOOT PROTECTOR

CROSS-REFERENCE TO RELATED APPLICATIONS

This application claims the benefit of U.S. Provisional Patent Application Ser. No. 60/300,213 filed on Jun. 22, 2001, now abandoned.

BACKGROUND OF THE INVENTION

The present invention relates generally to a medical boot-style foot protector for a bedridden patient and more particularly, to a foot protector that is padded and textile enclosed which wraps around the patient's foot and lower calf.

Bedridden patients are often located in nursing homes and hospital rooms as well as in their own homes. Many of these patients suffer from lower leg and foot complications, such as with diabetes and arterial disease. After surgery or during a period of bed rest convalescence, a patient may be immobilized for an extended period of time. Bedridden individuals may experience ulcerative conditions (pressure sores) on the skin and underlying tissues and bone of the ankles, feet, heels and toes as a result of extended contact of the skin with bedding materials. There are many types of foot protectors on the market today that are used by these patients. These foot protectors range from the inexpensive, non-durable type to the expensive, bulky type that are very heavy and difficult to use or walk on.

SUMMARY OF THE INVENTION

The present invention provides a foot protector to be worn on the foot of a patient. The foot protector comprises a fabric body, a top opening in the fabric body for exposing an anterior portion of the patient's foot and lower leg, a strap for partially closing the top opening, a fastener for securing the strap across the top opening, a bottom opening for exposing a heel of the patient's foot, and a toe flap adjacent the top opening for alternately supporting and covering toes of the patient's foot.

According to another aspect, the present invention provides a foot protector to be worn on the foot of a patient. The foot protector comprises a fabric body and a generally wedge-shaped deformable block enclosed within the fabric body for supporting the calf of the patient, the block having a truncated peak forming a plateau for relieving an Achilles region of the patient's foot, and the block having a heel relief area so that the block does not apply pressure to the patient's heel.

DETAILED DESCRIPTION OF PRESENT EMBODIMENT

Figure 1:
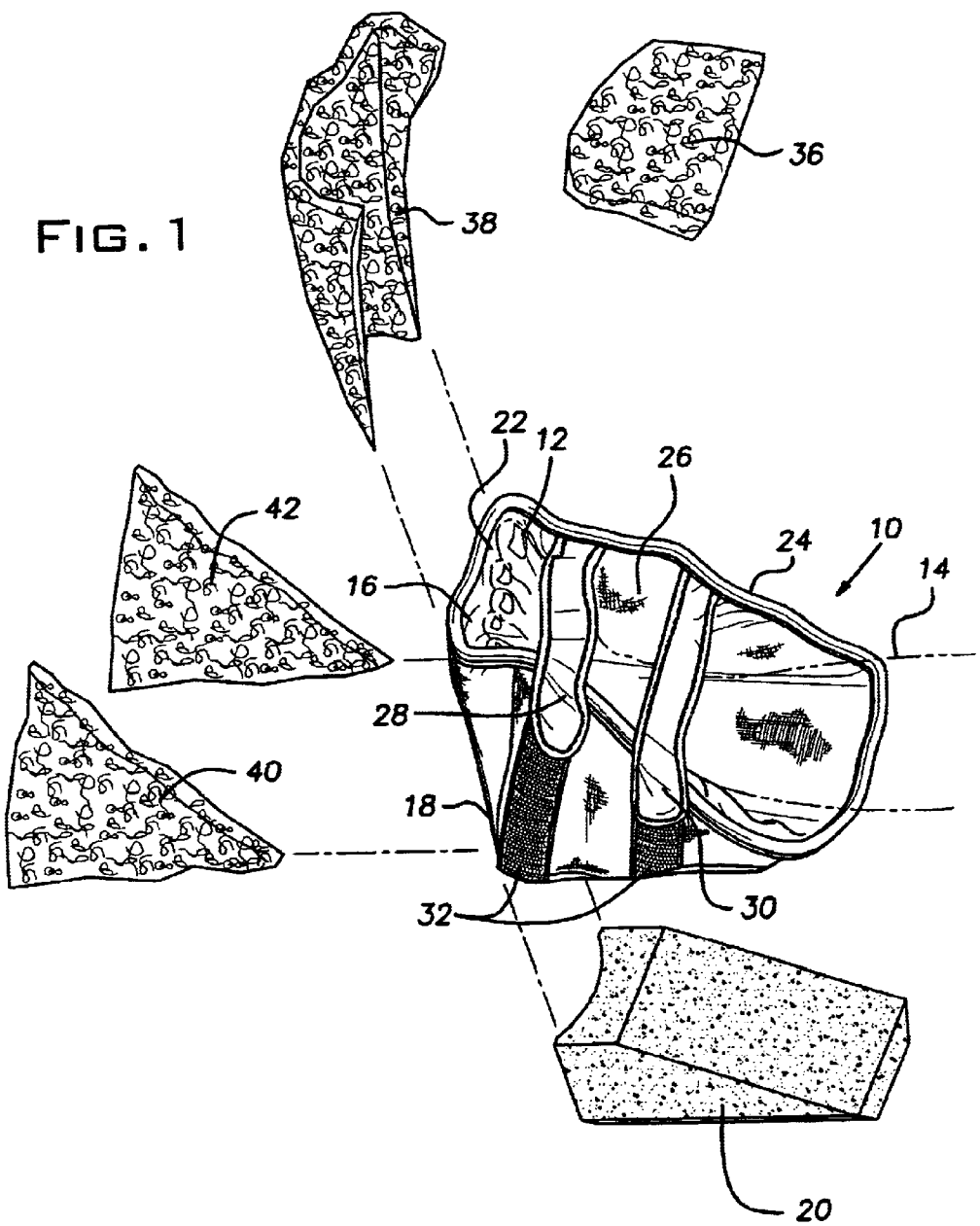
FIG. 1 is an exploded perspective view of the foot protector having a foot and leg of a wearer shown in phantom.
Figure 2:
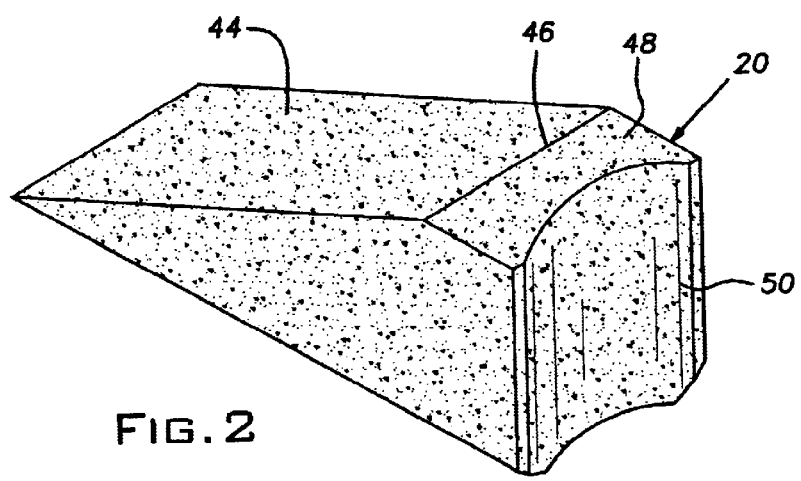
FIG. 2 is a perspective view of a modified wedge-shaped foam block.
Figure 3:
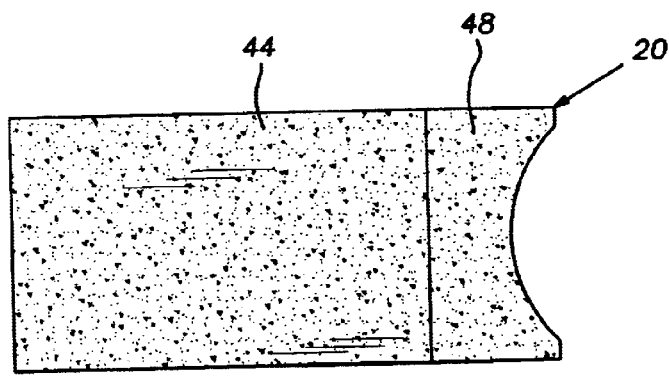
FIG. 3 is a top view of the modified wedge-shaped foam block.
Figure 4:
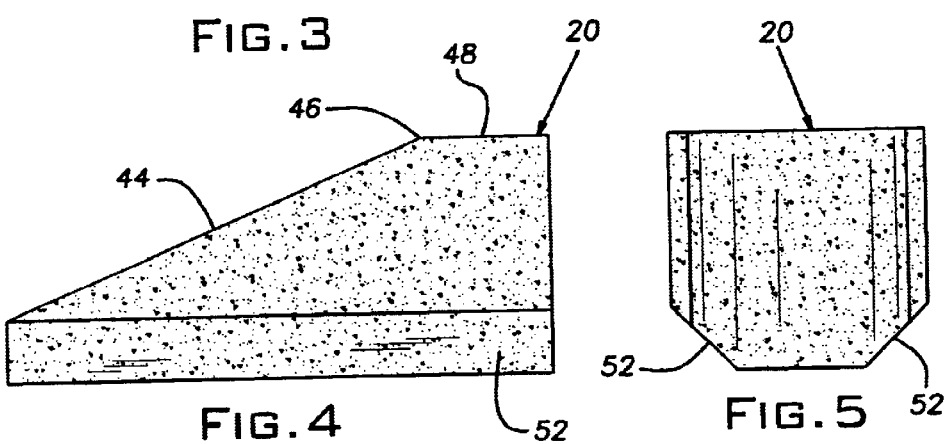
FIG. 4 is a side view of the modified wedge-shaped foam block.
Figure 6:
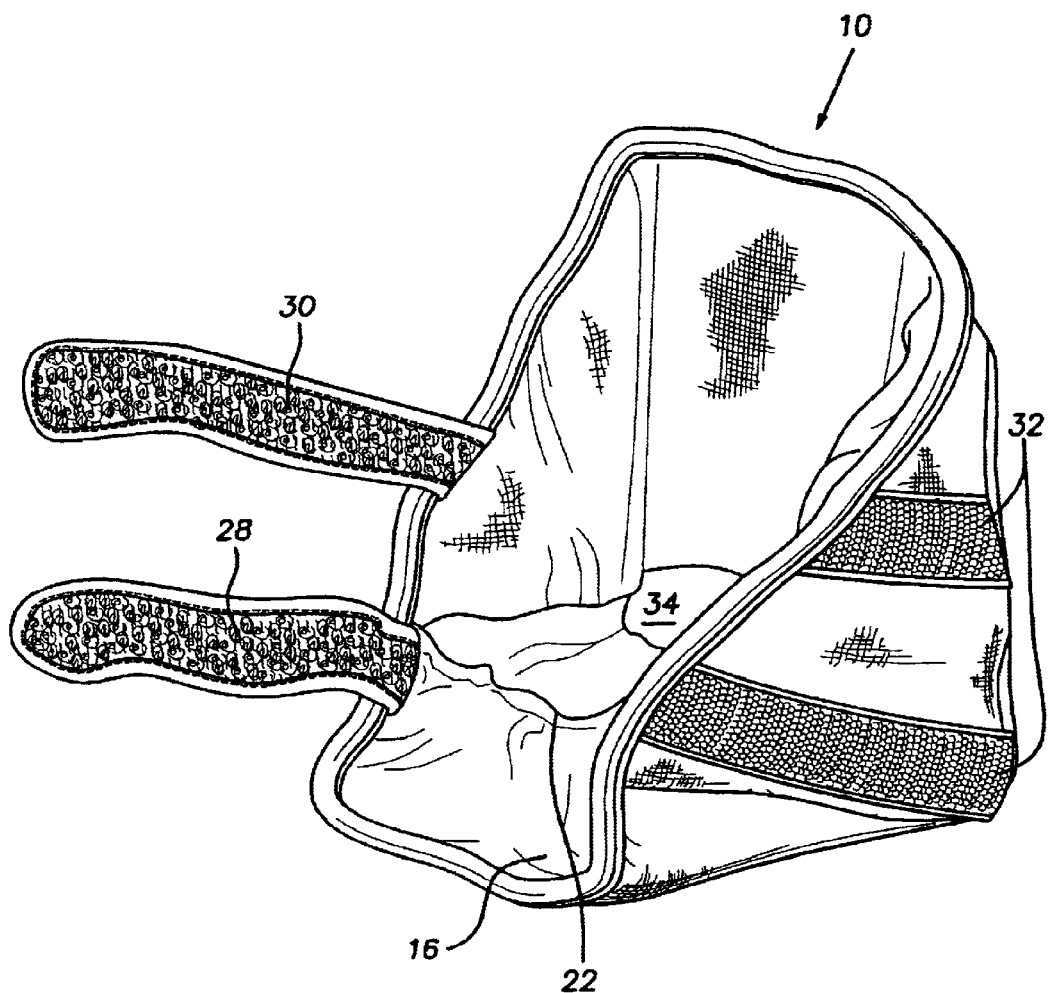
FIG. 6 is a perspective view of the foot protector illustrating the toe flap feature.

As shown in FIGS. 1 and 6, the present invention relates to a padded medical boot-style foot protector 10 that is worn around a patient's foot 12 and lower leg 14. The foot protector 10 includes a padded toe area 16, a padded ankle area 18 and generally wedge-shaped foam block 20 for padding and supporting the Achilles tendon area of a patient's foot. The wedge shaped foam block 20 also elevates and suspends the patient's heel to prevent decubitus pressure ulcers from forming on the bottom of the heel. The foot protector 10 further comprises a toe flap 22 capable of supporting a patient's foot 12 at an angle of 90 degrees or less with respect to the patient's lower leg 14.

As best shown in FIG. 1, the foot protector 10 comprises a body 24 of a textile web or other fabric or flexible material which wraps around the patient's foot 12 and lower leg 14. The body 24 of the foot protector 10 has a top opening 26, partially exposing the anterior parts of the lower leg 14 and foot 12. Two straps 28, 30 extend from one side of the foot protector and can be drawn across the top opening 24. The straps 28, 30 are held in place on the opposite side of the top opening 26 by means of fasteners, such as VELCRO or hook and loop style fasteners 32. Other fasteners, such as snaps, buckles, buttons or laces could alternatively be used. The straps 28, 30 partially close the top opening 26 by pulling the foot protector 10 snugly around the patient's foot. A bottom opening 34 is provided to expose the heel of the patient.

As illustrated in the exploded view of FIG. 1, sewn into the interior of the body 24 of the foot protector 10 is toe padding 36 adjacent to the toe area, bottom padding 38 for the bottom of the foot, ankle padding 40, 42 for both sides of the ankle area, and the generally wedge-shaped foam block 20. The padding 36–42 can be made from any suitable material, such as a batting material of natural or synthetic fibers, an open or closed cell foam material or other similar material. Rather than being sewn into the body 24, the padding 36–42 can be inserted into pockets defined by the body 24 without being secured thereto.

Referring now to FIGS. 2–5, the wedge-shaped foam block 20 is shown. The foam block 20 is constructed from a closed cell polyurethane foam or similar material. The foam block 20 is positioned inside the body 24 of the foot protector 10 so that a top face 44 slopes downward from the patients heel to the lower leg 14. The peak 46 of the sloping top face 44 is truncated, creating a small plateau 48 which reduces the pressure placed on the Achilles tendon region, helps to stabilize the foot, and elevates the foot a set distance, for example 3½ inches off of a bed surface while the patient is lying supine. An end surface 50 of the foam block 20 adjacent the plateau 48 is arched inward to comfortably accommodate the patient's heel. The arched end surface 50 helps to suspend the patient's heel above the bed surface without applying pressure to the heel itself.

Figure 5:
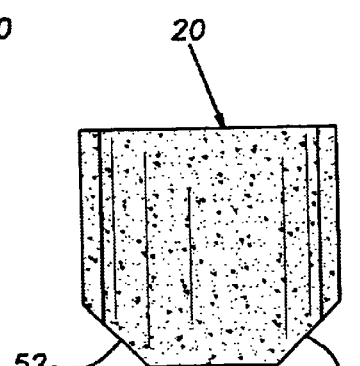
FIG. 5 is a front view of the modified wedge-shaped foam block.

As best shown in FIG. 5, the lower edge portion 52 of each side of the foam block 20 is chamfered or angled inward to compensate for any compression produced by the patient's foot and to allow for side-to-side roll of the foot protector 10, while reducing the likelihood of the foot protector 10 completely flipping on its side.

Referring now to FIG. 6, the toe flap 22 is provided at the end of the top opening 24 to cover the patient's toes. The toe flap 22 is padded and serves as a toe warmer. A padded toe section 16 serves as a kind of strap around the bottom of the foot provided within the portion of the foot protector 10 which covers the sole of the patient's foot. The padded toe section 16 is designed in such a way that it supports the patient's foot, pulling the foot and toes toward the patient's head. The design is specifically adapted to support the patient's foot 12 at an angle of 90 degrees or less with respect to the patient's lower leg 14.

Alternatively, the toe flap 22 can be positioned beneath the patient's toes, allowing the toes to be exposed. The toe flap 22 also provides additional support to the patient's foot when positioned beneath the toes. The toe flap 22 is sewn at an angle such that the patient's foot 12 is pulled up toward the patient's lower leg 14.

Although the invention has been shown and described with respect to certain embodiments, it is obvious that equivalent alterations and modifications will occur to others skilled in the art upon reading and understanding of the specification. The present invention includes all such equivalent alterations and modifications.

What is claimed is:

1. A foot protector to be worn on the foot of a patient, the foot protector comprising:
    a fabric body;
    a top opening in the fabric body for exposing an anterior portion of the patient's foot and lower leg;
    a strap for partially closing the top opening;
    a fastener for securing the strap across the top opening;
    a bottom opening for exposing a heel of the patient's foot; and
    a toe flap adjacent the top opening for alternately supporting and covering toes of the patient's foot.

2. The foot protector of claim 1, wherein the fabric body comprises a textile web.

3. The foot protector of claim 1, wherein the fastener comprises a hook and loop material.

4. The foot protector of claim 1, further comprising a generally wedge-shaped deformable block enclosed within the fabric body for supporting the calf of the patient, the block having a truncated peak forming a plateau for reducing pressure applied to an Achilles tendon region of the patient's foot, and the block having a heel relief recess so that the block does not apply pressure to the patient's heel.

5. The foot protector of claim 4, wherein two lower longitudinal edges of the block are chamfered.

6. A foot protector to be worn on the foot of a bedridden patient, the foot protector comprising:
    a fabric body; and
    a generally wedge-shaped deformable block enclosed within the fabric body for supporting the calf of the patient, the block having a truncated peak forming a plateau for reducing pressure applied to an Achilles tendon region of the patient's foot, and the block having a heel relief recess so that the block does not apply pressure to the patient's heel.

7. The foot protector of claim 6 further comprising:
    a top opening in the fabric body for exposing an anterior portion of the patient's foot and lower leg;
    a strap for partially closing the top opening;
    a fastener for securing the strap across the top opening; and
    a bottom opening for exposing a heel of the patient's foot.

8. The foot protector of claim 7, wherein the fastener comprises a hook and loop material.

9. The foot protector of claim 6, wherein two lower longitudinal edges of the block are chamfered.

10. The foot protector of claim 6, wherein the fabric body comprises a textile web.

* * * * *

UNITED STATES PATENT AND TRADEMARK OFFICE
CERTIFICATE OF CORRECTION

PATENT NO.     : 6,640,810 B1                                                         Page 1 of 1
DATED             : November 4, 2003
INVENTOR(S)  : Kevin Callsen et al.

It is certified that error appears in the above-identified patent and that said Letters Patent is hereby corrected as shown below:

Title page,
Item [56], References Cited, OTHER PUBLICATIONS, please delete "Nonambulatory leel ulceration", and insert therefor -- Nonambulatory heel ulceration --.

Column 2,
Line 17, please delete "textile web or", and insert therefor -- textile or --.

Signed and Sealed this

Twenty-fourth Day of February, 2004

JON W. DUDAS
*Acting Director of the United States Patent and Trademark Office*